US006228553B1

(12) United States Patent
Matsushita et al.

(10) Patent No.: US 6,228,553 B1
(45) Date of Patent: May 8, 2001

(54) PYRROLO [1,2-A] PYRIMIDINE COMPOUND AND HEAT-SENSITIVE RECORDING MATERIAL USING THE SAME

(75) Inventors: Tetsunori Matsushita; Naoto Yanagihara; Masanobu Takashima; Mitsuyuki Tsurumi, all of Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/349,364

(22) Filed: Jul. 8, 1999

(30) Foreign Application Priority Data

Jul. 14, 1998 (JP) .................................................. 10-199071

(51) Int. Cl.[7] .............................. G03C 1/58; C07D 239/70
(52) U.S. Cl. .......................... 430/179; 430/138; 430/171; 544/287; 544/293; 544/282
(58) Field of Search .................................... 430/179, 171, 430/138; 544/287, 282, 293

(56) References Cited

U.S. PATENT DOCUMENTS

| 3,857,838 | * | 12/1974 | Perronnet et al. | 260/243 R |
| 4,367,229 | * | 1/1983 | Kokosi et al. | 544/282 |
| 5,925,489 | * | 7/1999 | Kawabuchi et al. | 430/138 |
| 6,060,206 | * | 5/2000 | Hanaki et al. | 430/179 |

FOREIGN PATENT DOCUMENTS

| 6-130600 | 5/1994 | (JP) | ................................. G03C/7/38 |

OTHER PUBLICATIONS

"UV–Fixable Diazo Type Thermal Recording Material", USAMI, et al., Denshi Shashin Gakkai Shi (Journal of the Electronic Photographic Society), vol. 26, No. 2, (1987), pp. 115 to 119).

"Mechanism of Color Developement for UV–Fixable Thermal Recording Material", Yoshida, et al. Denshi Shashin Gakkai Shi (Journal of Electronic Photographic Society), vol. 26, No. 2, (1987), pp. 121 to 125).

* cited by examiner

Primary Examiner—John S. Chu
(74) Attorney, Agent, or Firm—Sughrue, Mion, Zinn, Macpeak & Seas, PLLC

(57) ABSTRACT

A pyrrolo[1,2-a]pyrimidine compound providing an excellent color-forming property is provided. Further, a novel cyan color-forming type diazo heat-sensitive recording material having excellent shelf life, image light-resistance and image fixing property is provided. The pyrrolo[1,2-a]pyrimidine compound is represented by following general formula (1). The heat-sensitive recording material comprises a substrate, and on the substrate, a heat-sensitive recording layer containing a diazonium salt compound and a coupler. The coupler contains at least one of pyrrolo[1,2-a]pyrimidine compounds represented by following general formula (1). In the formula, $R^1$ represents an aryl group or the like, $R^2$ represents an alkoxycarbonyl group or the like, $R^3$ and $R^4$ represent an acyl group or the like, and $R^5$ represents a hydrogen atom or the like.

General formula (1)

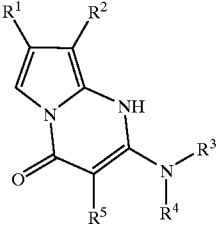

11 Claims, No Drawings

PYRROLO [1,2-A] PYRIMIDINE COMPOUND AND HEAT-SENSITIVE RECORDING MATERIAL USING THE SAME

BACKGROUND OF THE INVENTION

1. Field of the Invention

The present invention relates to a pyrrolo[1,2-a]pyrimidine compound useful as a coupler of a heat-sensitive recording material, and to a heat-sensitive recording material using a diazonium salt compound and the pyrrolo[1,2-a]pyrimidine compound coupler as color-developing components.

2. Description of the Related Art

As heat-sensitive recording materials become more high-performance, there is required a heat-sensitive recording material which has cyan-color forming property, excellent color-forming property, long shelf life, improved storability of images and an improved image fixing property.

Diazonium salt compounds are compounds having very high chemical activity, and easily react with compounds called couplers (e.g., phenol derivatives, compounds having an active methylene group) to form an azo dye, and also are light-sensitive and lose their activity when decomposed due to irradiation by light. Therefore, diazonium salt compounds have been used as light recording materials such as bydiazo copies (see, "*Shashin Kogaku no Kiso, Higinen Shashin Hen* (Fundamentals of Photographic Technology, Non-Silver Salt Photography Volume)" edited by Nippon Shashin Gakkai (Japan Photographic Society), Corona Co. (1982), pp. 89 to 117, and 182 to 201).

Further, by utilizing the property of diazonium salt compounds that they lose their activity due to decomposition by light, diazonium salt compounds have recently been used in recording materials which require fixing of images. As an example, there has been proposed a light fixing type heat-sensitive recording material in which a diazonium salt compound and a coupler are heated in accordance with image signals and react to form images, and thereafter, the images are fixed by irradiation of light (Hirotsugu Sato et al., "*GazoDenshi Gakkai Shi* (Journal of the Image Electronics Society)", Vol. 11, No. 4 (1982), pp. 290–296).

However, these recording materials using as a color-forming element a diazonium salt compound have a drawback in that the activity of the diazonium salt compound is extremely high, and even in dark places, the diazonium salt compound thermally decomposes gradually such that the reactivity thereof is lost, and therefore, its shelf life as a recording material is short. As one means for improving this drawback, there is a method in which a diazonium salt compound is encapsulated in microcapsules. It has become possible by this method to isolate the diazonium salt compound from substances promoting decomposition such as water, bases and the like, and to greatly improve the shelf life as a recording material (Tomomasa Usami et al., "*Denshi Shashin Gakkai Shi* (Journal of the Electronic Photographic Society)", Vol. 26, No. 2, (1987), pp. 115 to 125).

When the microcapsule is a microcapsule having a wall which has a glass transition temperature and in which the glass transition temperature is somewhat higher than room temperature such as urea resins and urethane resins, this capsule is called a heat-responsive microcapsule and is useful as a heat-sensitive recording material since, at room temperature, the capsule wall exhibits non-permeability with respect to substances and, at glass transition temperature or higher, exhibits permeability with respect to substances.

Namely, if a heat-sensitive recording layer comprising heat-responsive microcapsules containing a diazonium salt compound, a coupler and a base is applied onto a substrate to form a recording material, the diazonium salt compound can be kept stable for a long period of time, a color-formed image can be easily formed by heating, and further, the image can be fixed by irradiation by light.

As described above, it has become possible to greatly improve the stability of a diazonium salt compound by encapsulating the compound in microcapsules.

On the other hand, it is known that when 2-hydroxy-3-naphtoic anilides are used as couplers, they are excellent as heat-sensitive recording color-forming materials, and if a coupling reaction is effected with a 4-substituted amino-2-alkoxybenzene diazonium salt compound, a blue dye can be formed (Japanese Patent Application Laid-Open (JP-A) No. 2-225082).

However, when a diazonium salt compound having $\lambda_{max}$ at a longer wavelength side is used, storability before use (ground coloring property during storage before copying) of the recording material deteriorates. Further, in the case of a diazonium salt compound having $\lambda_{max}$ at a shorter wavelength side, when the aforementioned 2-hydroxy-3-naphtoic anilides are used, there are drawbacks in that the fixing property of images when irradiated with light is hindered, the hue extends over a long wavelength even to cyan, and further, storability of color-developed images (light fastness) is not sufficient.

As described above, there has not been obtained a heat-sensitive recording material which has cyan color-forming property, results in excellent color-forming property, and has a saltiscactory shelf life, image storability and image fixing property, until now.

SUMMARY OF THE INVENTION

The present invention has been accomplished in view of the aforementioned, and an object thereof is to provide a pyrrolo[1,2-a]pyrimidine compound which is useful as a coupler providing an excellent color-forming property. Another object of the present invention is to provide a novel cyan color-forming type diazo heat-sensitive recording material which contains the pyrrolo[1,2-a]pyrimidine compound coupler and a diazonium salt compound and has excellent shelf life, image light-resistance and image fixing property in addition to the above-described properties.

The present inventors have studied couplers intensively, and have found that a novel pyrrolo[1,2-a]pyrimidine compound represented by the following general formula (1) is useful as a coupler which provides an excellent color-forming property. Further, the present inventors have found that a heat-sensitive recording material using the pyrrolo[1,2-a]pyrimidine compound and a diazonium salt compound which will be described below has improved shelf life, image light-resistance and image fixing property, and has an excellent cyan color-forming property. Thus, the present inventors invented.

The present invention provides a pyrrolo[1,2-a]pyrimidine compound represented by following general formula (1):

General formula (1)

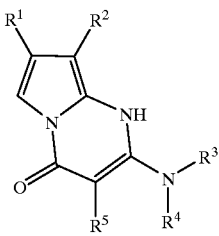

(wherein, in general formula (1), $R^1$ represents an aryl group, alkyl group, carbamoyl group, alkoxycarbonyl group or aryloxycarbonyl group; $R^2$ represents an alkoxycarbonyl group, aryloxycarbonyl group or cyano group; $R^3$ and $R^4$ each independently represents a hydrogen atom, aryl group, alkyl group, acyl group, carbamoyl group, alkoxycarbonyl group, aryloxycarbonyl group, alkylsulfonyl group, arylsulfonyl group, sulfamoyl group, alkylphosphoryl group or arylphosphoryl group; $R^5$ represents a hydrogen atom, halogen atom, cyano group, acyl group, carbamoyl group, alkoxycarbonyl group, aryloxycarbonyl group, acyloxy group, sulfamoyl group, alkylsulfonyl group, arylsulfonyl group, alkylphosphoryl group or arylphosphoryl group).

Further, the present invention provides a heat-sensitive recording material comprising a substrate, and on said substrate, a heat-sensitive recording layer containing a diazonium salt compound and a coupler which forms color by reacting with the diazonium salt compound during heating, wherein the coupler contains at least one of the pyrrolo[1,2-a]pyrimidine compounds represented by said general formula (1).

DETAILED DESCRIPTION OF THE INVENTION

The pyrrolo[1,2-a]pyrimidine compound of the present invention will be described in detail hereinafter.

The pyrrolo[1,2-a]pyrimidine compound of the present invention has the feature that when it is coupled as a coupler with a diazonium salt compound, an excellent color-forming property is obtained and a dye having little yellow light absorption can be provided.

Specifically, this compound is a novel compound represented by general formula (1).

In the formula, $R^1$ represents an aryl group, alkyl group, carbamoyl group, alkoxycarbonyl group or aryloxycarbonyl group.

Of the substituents represented by $R^1$, the aryl group may be substituted by an alkyl group, alkoxy group, aryloxy group, halogen atom, nitro group, cyano group, substituted carbamoyl group, substituted sulfamoyl group, substituted amino group, substituted oxycarbamoyl group, substituted oxysulfonyl group, alkylthio group, arylthio group, alkylsulfonyl group, arylsulfonyl group, aryl group, hydroxy group, acyl group, acyloxy group, substituted sulfonyloxy group, substituted aminocarbonyloxy group, or substituted phosphoryloxy group.

When $R^1$ represents an aryl group, an aryl group having 6 to 30 carbon atoms is preferable. Examples thereof include a phenyl group, 2-methylphenyl group, 2-chlorophenyl group, 2-methoxyphenyl group, 2-ethoxyphenyl group, 2-propoxyphenyl group, 2-isopropoxyphenyl group, 2-butoxyphenyl group, 2-(2-ethylhexyloxy)phenyl group, 2-octyloxyphenyl group, 2-undecyloxyphenyl group, 2-trifluoromethylphenyl group, 2-(2-ethylhexyloxy)-5-chlorophenyl group, 2,2'-hexyloxy-3,5-dichlorophenyl group, 3-(2,4-di-t-pentylphenoxyethoxy)phenyl group, 2-(dibutylaminocarbonylethoxy)phenyl group, 2,4-dichlorophenyl group, 2,5-dichlorophenyl group, 2,4,6-trimethylphenyl group, 3-chlorophenyl group, 3-nitrophenyl group, 3-cyanophenyl group, 3-trifluoromethylphenyl group, 3-methoxyphenyl group, 3-ethoxyphenyl group, 3-butoxyphenyl group, 3-(2'-ethylhexyloxy)phenyl group, 3,4-dichlorophenyl group, 3,5-dichlorophenyl group, 3,4-dimethoxyphenyl group, 3,5-dibutoxyphenyl group, 3-octyloxyphenyl group, 3-(dibutylaminocarbonylmethoxy) phenyl group, 3-(di-2-ethylhexylaminocarbonylmethoxy) phenyl group, 3-dodecyloxyphenyl group, 4-chlorophenyl group, 4-cyanophenyl group, 4-nitrophenyl group, 4-trifluoromethylphenyl group, 4-methoxyphenyl group, 4-ethoxyphenyl group, 4-isopropoxyphenyl group, 4-butoxyphenyl group, 4-(2-ethylhexyloxy)phenyl group, 4-isopentyloxyphenyl group, 4-(octadecyloxy)phenyl group, 4-benzylphenyl group, 4-aminosulfonylphenyl group, 4-N,N-dibutylsulfonylphenyl group, 4-ethoxycarbonylphenyl group, 4-(2-ethylhexyloxycarbonyl)phenyl group, 4-t-octylphenyl group, 4-fluorophenyl group, 3-acetylphenyl group, 2-acetylaminophenyl group, 2,4-di-t-pentylphenyl group, 4-(2-ethylhexyloxy)carbonylphenyl group, 4-methylthiophenyl group, 4-(4-chlorophenylthio)phenyl group, hydroxyphenyl group, phenylsulfonylphenyl group, phenylsulfonyoxyphenyl group, phenylcarbonyloxyphenyl group, dimethylaminocarbonyloxyphenyl group, butylcarbonyloxyphenyl group and the like.

Of the substituents represented by $R^1$, the alkyl group may be linear or branched, and may have an unsaturated bond. Further, such an alkyl group may be substituted by an alkoxy group, aryloxy group, alkoxycarbonyl group, aryloxycarbonyl group, aryl group, hydroxy group, halogen atom or the like. This aryl group may further be substituted by an alkyl group, alkoxy group, nitro group, cyano group, hydroxy group or halogen atom.

When $R^1$ represents an alkyl group, an alkyl group having 1 to 30 carbon atoms is preferable. Examples thereof include a methyl group, trifluoromethyl group, ethyl group, butyl group, hexyl group, octyl group, 2-ethylhexyl group, decyl group, dodecyl group, octadecyl group, propyl group, isopropyl group, isobutyl group, sec-butyl group, t-butyl group, pentyl group, 1-ethylpentyl group, cyclopentyl group, cyclohexyl group, isopentyl group, heptyl group, nonyl group, undecyl group, propenyl group, heptadecenyl group, t-octyl group, ethoxycarbonylmethyl group, butoxycarbonylmethyl group, 2-ethylhexyloxycarbonylmethyl group, 1-(ethoxycarbonyl)ethyl group, 2',4'-diisopentylphenyloxymethyl group, 2',4'-di-t-butylphenyloxymethyl group, ethoxycarbonylethyl group, 2-ethylhexyloxycarbonylethyl group, butyldecyloxycarbonylethyl group, dibutylaminocarbonylmethyl group, dibenzylaminocarbonylethyl group, ethyloxycarbonylpropyl group, 2-ethylhexyloxycarbonylpropyl group, 2,4-di-t-amylphenyloxypropyl group, 1-(2',4'-di-t-amylphenyloxy) propyl group, 2,4-di-t-butylphenyloxypropyl group, acetylaminoethyl group, N,N-dihexylaminocarbonylethyl group, 2,4-di-t-amyloxyethyloxycarbonylpropyl group, isostearyloxycarbonylpropyl, 1-(2,4-di-t-pentylphenyloxy) propyl group, 2,4-di-t-pentylphenyloxyethyloxycarbonylpropyl group, naphthyloxyethyloxycarbonylethyl group, N-methyl-N-phenylethyloxycarbonylethyl group, methanesulfonylaminopropyl group and the like.

Of the substituents represented by $R^1$, the carbamoyl group may be a substituted or unsubstituted carbamoyl group. Examples thereof include a carbamoyl group, N-alkylcarbamoyl group, N-arylcarbamoyl group, N,N-dialkylcarbamoyl group, N,N-diarylcarbamoyl group, N-alkyl-N-arylcarbamoyl group and the like.

When $R^1$ represents a substituted carbamoyl group, a substituted carbamoyl group having 1 to 30 carbon atoms is preferable. Examples thereof include an N-methylcarbamoyl group, N-ethylcarbamoyl group, N-propylcarbamoyl group, N-butylcarbamoyl group, N-hexylcarbamoyl group, N-cyclohexylcarbamoyl group, N-octylcarbamoyl group, N-2-ethylhexylcarbamoyl group, N-decylcarbamoyl group, N-octadecylcarbamoyl group, N-phenylcarbamoyl group, N-2-methylphenylcarbamoyl group, N-2-chlorophenylcarbamoyl group, N-2-methoxyphenylcarbamoyl group, N-2-chlorophenylcarbamoyl group, N-2-methoxyphenylcarbamoyl group, N-2-isopropoxyphenylcarbamoyl group, N-2-(2-ethylhexyloxy)phenylcarbamoyl group, N-3-chlorophenylcarbamoyl group, N-3-nitrophenylcarbamoyl group, N-3-cyanophenylcarbamoyl group, N-4-methoxycarbamoyl group, N-4-(2'-ethylhexyloxy)phenylcarbamoyl group, N-4-cyanophenylcarbamoyl group, N-methyl-N-phenylcarbamoyl group, N,N-dimethylcarbamoyl group, N,N-dibutylcarbamoyl group, N,N-diphenylcarbamoyl group and the like.

Of the substituents represented by $R^1$, an alkoxycarbonyl group having 2 to 20 carbon atoms is preferable as the alkoxycarbonyl group. Examples thereof include a methoxycarbonyl group, ethoxycarbonyl group, propoxycarbonyl group, butoxycarbonyl group, hexyloxycarbonyl group, 2-ethylhexyloxycarbonyl group, octyloxycarbonyl group, decyloxycarbonyl group, octadecyloxycarbonyl group, phenyloxyethyloxycarbonyl group, phenyloxypropyloxycarbonyl group, 2,4-di-t-amylphenyloxyethylcarbonyl group, 2,6-di-t-butyl-4-methylcyclohexyloxycarbonyl group, isostearyloxycarbonyl group and the like.

Of the substituents represented by $R^1$, an aryloxycarbonyl group having 7 to 30 carbon atoms is preferable as the aryloxycarbonyl group. Examples thereof include a 2-methylphenyloxycarbonyl group, 2-chlorophenyloxycarbonyl group, 2,6-dimethylphenyloxycarbonyl group, 2,4,6-trimethylphenyloxycarbonyl group, 2-methoxyphenyloxycarbonyl group, 2-butoxyphenyloxycarbonyl group, 3-cyanophenyloxycarbonyl group, 3-nitrophenyloxycarbonyl group, 2,2-ethylhexylphenyloxycarbonyl group, 3-(2-ethylhexyloxy)phenyloxycarbonyl group, 4-fluorophenyloxycarbonyl group, 4-chlorophenyloxycarbonyl group, 4-cyanophenyloxycarbonyl group, 4-butoxyphenyloxycarbonyl group and the like.

Aryl group and alkyl group are preferable substituents represented by $R^1$, and an aryl group is particularly preferable.

$R^2$ represents an alkoxycarbonyl group, aryloxycarbonyl group or cyano group.

Of the substituents represented by $R^2$, an alkoxycarbonyl group having 2 to 20 carbon atoms is preferable as the alkoxycarbonyl group, and examples thereof include a methoxycarbonyl group, ethoxycarbonyl group, propoxycarbonyl group, butoxycarbonyl group, hexyloxycarbonyl group, 2-ethylhexyloxycarbonyl group, octyloxycarbonyl group, decyloxycarbonyl group, octadecyloxycarbonyl group, phenyloxyethyloxycarbonyl group, phenyloxypropyloxycarbonyl group, 2,4-di-t-amylphenyloxyethylcarbonyl group, 2,6-di-t-butyl-4-methylcyclohexyloxycarbonyl group, isostearyloxycarbonyl group and the like.

Of the substituents represented by $R^2$, an aryloxycarbonyl group having 7 to 30 carbon atoms is preferable as the aryloxycarbonyl group, and examples thereof include a 2-methylphenyloxycarbonyl group, 2-chlorophenyloxycarbonyl group, 2,6-dimethylphenyloxycarbonyl group, 2,4,6-trimethylphenyloxycarbonyl group, 2-methoxyphenyloxycarbonyl group, 2-butoxyphenyloxycarbonyl group, 3-cyanophenyloxycarbonyl group, 3-nitrophenyloxycarbonyl group, 2,2-ethylhexylphenyloxycarbonyl group, 3-(2-ethylhexyloxy)phenyloxycarbonyl group, 4-fluorophenyloxycarbonyl group, 4-chlorophenyloxycarbonyl group, 4-cyanophenyloxycarbonyl group, 4-butoxyphenyloxycarbonyl group and the like.

$R^3$ and $R^4$ each independently represents a hydrogen atom, aryl group, alkyl group, acyl group, carbamoyl group, alkoxycarbonyl group, aryloxycarbonyl group, alkylsulfonyl group, arylsulfonyl group, sulfamoyl group, alkylphosphoryl group or arylphosphoryl group.

Of the substituents represented by $R^3$ and $R^4$, an aryl group having 6 to 30 atoms is preferable as the aryl group, and examples thereof include a phenyl group, 2-methylphenyl group, 2-chlorophenyl group, 2-methoxyphenyl group, 2-ethoxyphenyl group, 2-propoxyphenyl group, 2-isopropoxyphenyl group, 2-butoxyphenyl group, 2-(2-ethylhexyloxy)phenyl group, 2-octyloxyphenyl group and the like.

Of the substituents represented by $R^3$ and $R^4$, the alkyl group may be linear or branched, and may have an unsaturated bond.

As the alkyl group, an alkyl group having 1 to 30 carbon atoms is preferable, and examples thereof include a methyl group, trifluoroethyl group, ethyl group, butyl group, hexyl group, octyl group, 2-ethylhexyl group, decyl group, dodecyl group, octadecyl group, propyl group, isopropyl group, isobutyl group, sec-butyl group, t-butyl group, pentyl group, 1-ethylpentyl group, cyclopentyl group, cyclohexyl group, isopentyl group, heptyl group, nonyl group, undecyl group, propenyl group, heptadecenyl group, t-octyl group, ethoxycarbonylmethyl group, butoxycarbonylmethyl group, 2-ethylhexyloxycarbonylmethyl group and the like.

Of the substituents represented by $R^3$ and $R^4$, an acyl group having 2 to 20 carbon atoms is preferable as the acyl group, and examples thereof include an acetyl group, propanoyl group, butanoyl group, pivaloyl group, hexanoyl group, octanoyl group, 2-ethylhexanoyl group, decanoyl group, dodecanoyl group, octadecanoyl group, 2-cyanopropanyl group, 1,1-dimethylpropanoyl group and the like.

The following are further examples of the acyl group.

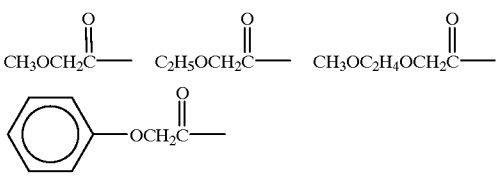

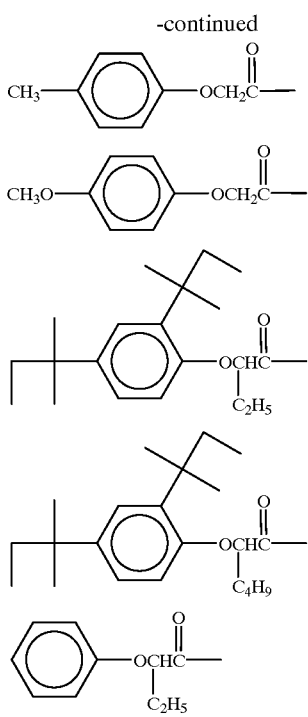

Of the substituents represented by $R^3$ and $R^4$, the carbamoyl group may be a substituted or unsubstituted carbamoyl group, and examples thereof include carbamoyl group, N-alkylcarbamoyl group, N-arylcarbamoyl group, N,N-dialkylcarbamoyl group, N,N-diarylcarbamoyl group, N-alkyl-N-arylcarbamoyl group and the like.

As the substituted carbamoyl group, a substituted carbamoyl group having 1 to 30 carbon atoms is preferable, and examples thereof include an N-methylcarbamoyl group, N-ethylcarbamoyl group, N-propylcarbamoyl group, N-butylcarbamoyl group, N-hexylcarbamoyl group, N-cyclohexylcarbamoyl group, N-octylcarbamoyl group, N-2-ethylhexylcarbamoyl group, N-decylcarbamoyl group, N-octadecylcarbamoyl group, N-phenylcarbamoyl group, N-2-methylphenylcarbamoyl group, N-2-chlorophenylcarbamoyl group, N-2-methoxyphenylcarbamoyl group, N-2-isopropoxyphenylcarbamoyl group, N-2-(2-ethylhexyloxy)phenylcarbamoyl group, N-3-chlorophenylcarbamoyl group, N-3-nitrophenylcarbamoyl group, N-3-cyanophenylcarbamoyl group, N-4-methoxycarbamoyl group, N-4-(2'-ethylhexyloxy)phenylcarbamoyl group, N-4-cyanophenylcarbamoyl group, N-methyl-N-phenylcarbamoyl group, N,N-dimethylcarbamoyl group, N,N-dibutylcarbamoyl group, N,N-diphenylcarbamoyl group and the like.

Of the substituents represented by $R^3$ and $R^4$, an alkoxycarbonyl group having 2 to 20 carbon atoms is preferable as the alkoxycarbonyl group, and examples thereof include a methoxycarbonyl group, ethoxycarbamoyl group, propoxycarbonyl group, butoxycarbonyl group, hexyloxycarbonyl group, 2-ethylhexyloxycarbonyl group, octyloxycarbonyl group, decyloxycarbonyl group, octadecyloxycarbonyl group, phenyloxyethyloxycarbonyl group, phenyloxypropyloxycarbonyl group, 2,4-di-t-amylphenyloxyethylcarbonyl group, 2,6-di-t-butyl-4-methylcyclohexyloxycarbonyl group, isostearyloxycarbonyl group and the like.

Of the substituents represented by $R^3$ and $R^4$, an aryloxycarbonyl group having 7 to 30 carbon atoms is preferable as the aryloxycarbonyl group, and examples thereof include a 2-methylphenyloxycarbonyl group, 2-chlorophenyloxycarbonyl group, 2,6-dimethylphenyloxycarbonyl group, 2,4,6-trimethylphenyloxycarbonyl group, 2-methoxyphenyloxycarbonyl group, 2-butoxyphenyloxycarbonyl group, 3-cyanophenyloxycarbonyl group, 3-nitrophenyloxycarbonyl group, 2,2-ethylhexylphenyloxycarbonyl group, 3-(2-ethylhexyloxy)phenyloxycarbonyl group, 4-fluorophenyloxycarbonyl group, 4-chlorophenyloxycarbonyl group, 4-cyanophenyloxycarbonyl group, 4-butoxyphenyloxycarbonyl group and the like.

Of the substituents represented by $R^3$ and $R^4$, the sulfamoyl group may be a substituted or unsubstituted sulfamoyl group, and examples thereof include a sulfamoyl group, N-alkylsulfamoyl group, N-arylsulfamoyl group, N,N-dialkylsulfamoyl group, N,N-diarylsulfamoyl group, N-alkyl-N-arylsulfamoyl group and the like.

Of the substituents represented by $R^3$ and $R^4$, a substituted sulfamoyl group having 0 to 30 carbon atoms is preferable as the substituted sulfamoyl group, and examples thereof include an N-methylsulfamoyl group, N-ethylsulfamoyl group, N-propylsulfamoyl group, N-butylsulfamoyl group, N-hexylsulfamoyl group, N-cyclohexylsulfamoyl group, N-octylsulfamoyl group, N-2-ethylhexylsulfamoyl group, N-decylsulfamoyl group, N-octadecylsulfamoyl group, N-phenylsulfamoyl group, N-2-methylphenylsulfamoyl group, N-2-chlorophenylsulfamoyl group, N-2-methoxyphenylsulfamoyl group, N-2-isopropoxyphenylsulfamoyl group, N-2-(2-ethylhexyloxy)phenylsulfamoyl group, N-3-chlorophenylsulfamoyl group, N-3-nitrophenylsulfamoyl group, N-3-cyanophenylsulfamoyl group, N-4-methoxysulfamoyl group, N-4-(2'-ethylhexyloxy)phenylsulfamoyl group, N-4-cyanophenylsulfamoyl group, N-methyl-N-phenylsulfamoyl group, N,N-dimethylsulfamoyl group, N,N-dibutylsulfamoyl group, N,N-diphenylsulfamoyl group, N,N-di-(2-ethylhexyl)sulfamoyl group and the like.

Of the substituents represented by $R^3$ and $R^4$, an alkylsulfonyl group having 1 to 20 carbon atoms is preferable as the alkylsulfonyl group, and examples thereof include a methylsulfonyl group, ethylsulfonyl group, propoxysulfonyl group, isopropylsulfonyl group, butylsulfonyl group, hexylsulfonyl group, cyclohexylsulfonyl group, octylsulfonyl group, 2-ethylhexylsulfonyl group, decanoylsulfonyl group, dodecanoylsulfonyl group, octadecanoylsulfonyl group, cyanomethylsulfonyl group and the like.

Of the substituents represented by $R^3$ and $R^4$, an arylsulfonyl group having 6 to 30 carbon atoms is preferable as the arylsulfonyl group, and examples thereof include a phenylsulfinyl group, 1-naphthylsulfonyl group, 2-naphthylsulfonyl group, 2-chlorophenylsulfonyl group, 4-methylphenylsulfonyl group, 4-methoxyphenylsulfonyl group, 2-methylphenylsulfonyl group, 2-methoxyphenylsulfonyl group, 2-butoxyphenylsulfonyl group, 3-chlorophenylsulfonyl group, 3-trifluoromethylphenylsulfonyl group, 3-cyanophenylsulfonyl group, 3-(2-ethylhexyloxy)phenylsulfonyl group, 3-nitrophenylsulfonyl group, 4-fluorophenylsulfonyl group, 4-cyanophenylsulfonyl group, 4-butoxyphenylsulfonyl group, 4-(2-ethylhexyloxy)phenylsulfonyl group, 4-octadecylphenylsulfonyl group and the like.

The following are further examples of the arylsulfonyl group.

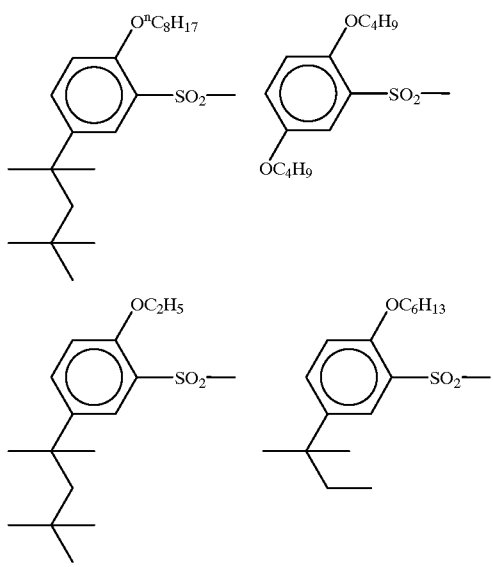

Of the substituents represented by $R^3$ and $R^4$, an alkylphosphoryl group having 2 to 40 carbon atoms is preferable as the alkylphosphoryl group, and examples thereof include a methylphosphoryl group, ethylphosphoryl group, propylphosphoryl group, isopropylphosphoryl group, butylphosphoryl group, isobutylphosphoryl group, sec-butylphosphoryl group, t-butylphosphoryl group, pentylphosphoryl group, isopentylphosphoryl group, hexylphosphoryl group, heptylphosphoryl group, octylphosphoryl group, 2-ethylhexylphosphoryl group, decylphosphoryl group, dodecylphosphoryl group, octadecylphosphoryl group, ethoxycarbonylmethylphosphoryl group, 2-ethylhexyloxycarbonylmethylphosphoryl group, aminocarbonylmethylphosphoryl group, N,N-dibutylaminocarbonylmethylphosphoryl group, N-methylaminocarbonylmethylphosphoryl group, N-ethylaminocarbonylmethylphosphoryl group, N-octylaminocarbonylmethylphosphoryl group, benzylphosphoryl group and the like.

Of the substituents represented by $R^3$ and $R^4$, an arylphosphoryl group having 12 to 50 carbon atoms is preferable as the arylphosphoryl group, and examples thereof include a phenylphosphoryl group, 1-naphthylphosphoryl group, 2-naphthylphosphoryl group, 2-chlorophenylphosphoryl group, 2-methylphenylphosphoryl group, 2-methoxyphenylphosphoryl group, 2-butoxyphenylphosphoryl group, 3-chlorophenylphosphoryl group, 3-trifluoromethylphenylphosphoryl group, 3-cyanophenylphosphoryl group, 3-(2-ethylhexyloxy)phenylphosphoryl group, 3-nitrophenylphosphoryl group, 4-fluorophenylphosphoryl group, 4-cyanophenylphosphoryl group, 4-butoxyphenylphosphoryl group, 4-(2-ethylhexyloxy)phenylphosphoryl group, 4-octadecylphenylphosphoryl group and the like.

Examples of preferable substituents represented by $R^3$ and $R^4$ are an acyl group, carbamoyl group, alkoxycarbonyl group, aryloxycarbonyl group and arylsulfonyl group, and an acyl group, carbamoyl group and alkoxycarbonyl group are particularly preferable substituents. It is preferable that at least one of $R^3$ and $R^4$ is a hydrogen atom.

$R^5$ represents a hydrogen atom, halogen atom, cyano group, acyl group, carbamoyl group, alkoxycarbonyl group, aryloxycarbonyl group, acyloxy group, sulfamoyl group, alkylsulfonyl group, arylsulfonyl group, alkylphosphoryl group or arylphosphoryl group.

Of the substituents represented by $R^5$, an acyloxy group having 2 to 20 carbon atoms is preferable as the acyloxy group, and examples thereof include an acetyloxy group, propanoyloxy group, butanoyloxy group, pentanoyloxy group, trifluoromethylcarbonyloxy group, octanoyloxy group, decanoyloxy group, undecanoyloxy group, octadecanoyloxy group and the like.

Of the substituents represented by $R^5$, the acyl group, carbamoyl group, alkoxycarbonyl group, aryloxycarbonyl group, alkylsulfonyl group, arylsulfonyl group, sulfamoyl group, alkylphosphoryl group and arylphosphoryl group are the same as defined for $R^3$ and $R^4$.

Examples of preferable substituents represented by $R^5$ are a hydrogen atom and a halogen atom, and a hydrogen atom is particularly preferable.

Specific, typical examples of the pyrrolo[1,2-a]pyrimidine compound represented by general formula (1) of the present invention are the following compounds. However, it is to be noted that the pyrrolo[1,2-a]pyrimidine of the present invention is not limited to these examples.

$R^1$ to $R^5$ in the following Tables 1 to 5 represent $R^1$ to $R^5$ in the above-described general formula (1).

TABLE 1

| No. | $R^1$ | $R^2$ | $R^3$ | $R^4$ | $R^5$ |
|---|---|---|---|---|---|
| (1) | —⟨phenyl⟩ | —CN | —C(=O)—CH(C₄H₉)— | —H | —H |
| (2) | —⟨phenyl⟩ | —CN | —C(=O)—C(CH₃)₃ | —H | —H |

TABLE 1-continued

| No. | R¹ | R² | R³ | R⁴ | R⁵ |
|---|---|---|---|---|---|
| (3) | phenyl | —CN | —C(=O)CH(C₂H₅)O—(2-tert-pentyl-4-tert-pentylphenyl) | —H | —H |
| (4) | phenyl | —CN | —C(=O)O—CH₂CH(C₂H₅)C₄H₉ | —H | —H |
| (5) | phenyl | —CN | —C(=O)NH—CH₂CH(C₂H₅)C₄H₉ | —H | —H |
| (6) | phenyl | —CN | —C(=O)N(C₄H₉)₂ | —H | —H |
| (7) | 2-methylphenyl | —CN | —C(=O)CH(C₂H₅)C₄H₉ | —H | —Cl |
| (8) | 2-fluorophenyl | —CN | —C(=O)O—CH(C₂H₅)C₅H₁₁ | —H | —H |
| (9) | 4-methylphenyl | —CN | —C(=O)C₃H₇ | —H | —H |
| (10) | 3-methylphenyl | —CN | —C(=O)CH₂O—phenyl | —H | —H |

TABLE 2

| No. | R¹ | R² | R³ | R⁴ | R⁵ |
|---|---|---|---|---|---|
| (11) | —CH₃ | —CN | —C(=O)CH(C₄H₉)O—(2-tert-pentyl-4-tert-pentylphenyl) | —H | —H |

TABLE 2-continued
| No. | R¹ | R² | R³ | R⁴ | R⁵ |
|---|---|---|---|---|---|
| (12) | 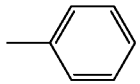 | —CN | 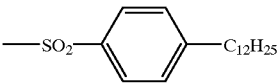 | —H | —H |
| (13) | 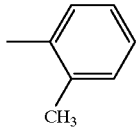 | —CN | 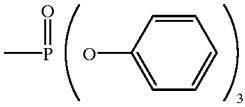 | —H | —H |
| (14) | 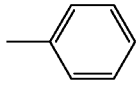 | —CN | 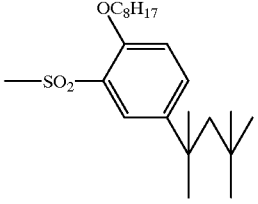 | —H | —H |
| (15) | 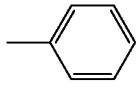 | —CN |  |  | —H |
| (16) | 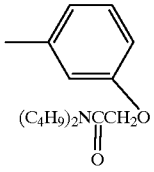 | —CN | 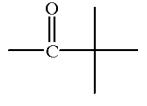 | —H | —H |
| (17) | 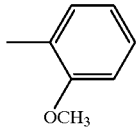 | —CN |  |  | —H |
| (18) | 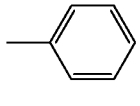 | —COOEt | 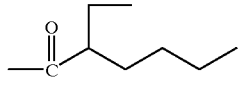 | —H | —H |
| (19) | 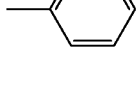 | —COOEt | 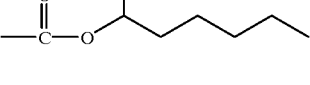 | —H | —H |
| (20) | 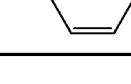 | —COOEt | 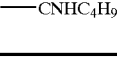 | —H | —H |
TABLE 3
| No | R¹ | R² | R³ | R⁴ | R⁵ |
|---|---|---|---|---|---|
| (21) | 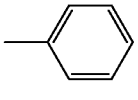 | —COOEt |  | —H | —H |

TABLE 3-continued
| No | R¹ | R² | R³ | R⁴ | R⁵ |
|---|---|---|---|---|---|
| (22) | 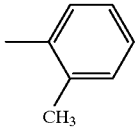 | —COOCH₃ | $\underset{\|}{-\overset{O}{\overset{\|}{C}}}CC_2H_5$ | —H | —Cl |
| (23) | 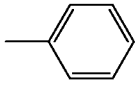 | —COOCH(CH₃)₂ | $-\overset{O}{\overset{\|}{C}}C(CH_3)_3$ | —H | —H |
| (24) | 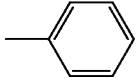 | —COOC(CH₃)₃ | $-\overset{O}{\overset{\|}{C}}OCH_3$ | —H | —H |
| (25) | 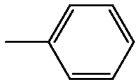 | | $-\overset{O}{\overset{\|}{C}}OCH_3$ | —H | —H |
| (26) | 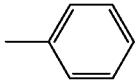 | | $-\overset{O}{\overset{\|}{C}}C_3H_7$ | —H | —H |
| (27) | 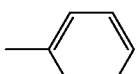 | | $-\overset{O}{\overset{\|}{C}}CH_3$ | —H | —H |
| (28) | 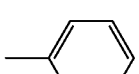 | | $-\overset{O}{\overset{\|}{C}}C_6H_5$ | —H | —H |

TABLE 3-continued

| No | R¹ | R² | R³ | R⁴ | R⁵ |
|---|---|---|---|---|---|
| (29) | phenyl | 2,6-di-tert-butyl-4-methylcyclohexyl (with —COO— linker, H) | —C(=O)—CH(C₂H₅)—C₄H₉ | —H | —H |
| (30) | phenyl | 2,6-di-tert-butyl-4-methylcyclohexyl (with —COO— linker, H) | —C(=O)—O—CH₂—CH(C₂H₅)—C₄H₉ | —H | —H |

TABLE 4

| No. | R¹ | R² | R³ | R⁴ | R⁵ |
|---|---|---|---|---|---|
| (31) | phenyl | 2,6-di-tert-butyl-4-methylcyclohexyl (with —COO— linker, H) | —C(=O)—NH—CH₂—CH(C₂H₅)—C₄H₉ | —H | —H |
| (32) | phenyl | 2,6-di-tert-butyl-4-methylcyclohexyl (with —COO— linker, H) | —C(=O)N(C₄H₉)₂ | —H | —H |
| (33) | phenyl | 2,6-di-tert-butyl-4-methylcyclohexyl (with —COO— linker, H) | —SO₂—(2-OC₈H₁₇-5-tert-pentyl-phenyl) | —H | —H |

TABLE 4-continued

| No. | R¹ | R² | R³ | R⁴ | R⁵ |
|---|---|---|---|---|---|
| (34) | 2-chlorophenyl | 2,6-di-tert-butyl-4-methylcyclohexyl ester (—COO—) | —C(=O)CH(C₂H₅)C₄H₉ | —H | —H |
| (35) | 3,4-dichlorophenyl | 2,6-di-tert-butyl-4-methylcyclohexyl ester (—COO—) | —C(=O)CH(C₂H₅)C₄H₉ | —H | —H |
| (36) | 4-chlorophenyl | 2,6-di-tert-butyl-4-methylcyclohexyl ester (—COO—) | —C(=O)CH(C₂H₅)C₄H₉ | —H | —H |
| (37) | 2-fluorophenyl | 2,6-di-tert-butyl-4-methylcyclohexyl ester (—COO—) | —C(=O)CH(C₂H₅)C₄H₉ | —H | —H |
| (38) | 4-chlorophenyl | 2,6-di-tert-butyl-4-methylcyclohexyl ester (—COO—) | —C(=O)O—CH₂CH(C₂H₅)C₄H₉ | —H | —H |
| (39) | 3,4-dichlorophenyl | 2,6-di-tert-butyl-4-methylcyclohexyl ester (—COO—) | —C(=O)C(CH₃)₃ | —H | —H |

TABLE 4-continued
| No. | R¹ | R² | R³ | R⁴ | R⁵ |
|---|---|---|---|---|---|
| (40) |  | 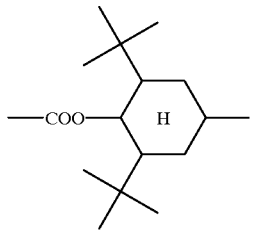 | 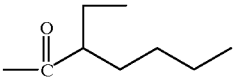 | —H | —Cl |
TABLE 5
| No. | R¹ | R² | R³ | R⁴ | R⁵ |
|---|---|---|---|---|---|
| (41) | 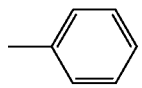 | 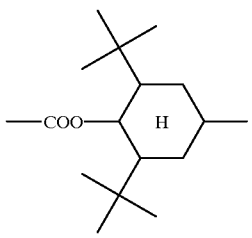 | 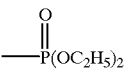 | —H | —H |
| (42) | 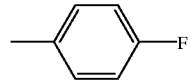 | 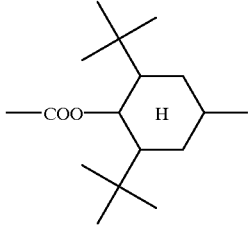 | 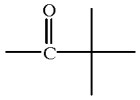 | —H | —H |
| (43) | 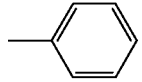 | —COOEt |  |  | —H |
| (44) | 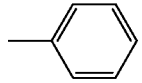 | 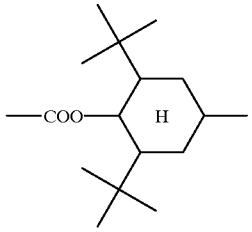 |  |  | —H |
| (45) | —CH₃ | 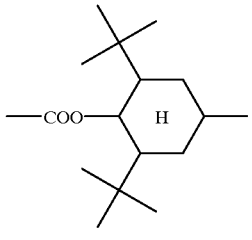 | 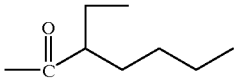 | —H | —H |

TABLE 5-continued

| No. | R¹ | R² | R³ | R⁴ | R⁵ |
|---|---|---|---|---|---|
| (46) | 4-chlorophenyl | —COOEt | —C(=O)CH(Et)(butyl) | —H | —H |
| (47) | 3,4-dichlorophenyl | —COOEt | —C(=O)CH(Et)(butyl) | —H | —H |

Method of Preparation

The pyrrolo[1,2-a]pyrimidine compound represented by general formula (1) of the present invention can be synthesized, for example, via a reaction route represented by the following formula.

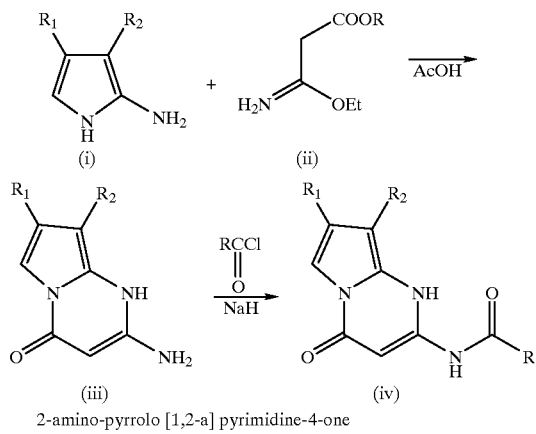

2-amino-pyrrolo [1,2-a] pyrimidine-4-one

The above reaction formula will be described in detail hereinafter. An α-aminoketone derivative is reacted with malonnitrile (R₂—CN) and cyano acetic acid derivative (R₂—COOR) according to a method of Carl Gehart et al., (Z. Chem., 1, 349, 1961) to be converted to a 2-aminopyrrole derivative (i). By using a method (Japanese Patent Application No.10-67442) using a phthalimide derivative instead of the α-aminoketone derivative, a 2-amino-pyrrole derivative is obtained at an even higher yield.

The resultant compound (i) and 3-ethoxy-3-iminopropionate (ii) are stirred at about 25 to 60° C. in a solvent which does not adversely influence this reaction (e.g., an alcohol such as methanol, ethanol or the like, or acetonitrile or the like) in the presence of an organic acid (for example, acetic acid, propionic acid or the like) to obtain 2-amino-pyrrolo[1,2-a]pyrimidine-4-one (iii).

The resultant compound (iii) is stirred at about 0 to 60° C. in the presence of an acid halide and sodium hydride in a solvent which does not adversely influence this reaction (for example, n,n-dimethylacetamide, tetrahydrofuran or the like) to obtain the pyrrolo[1,2-a]pyrimidine compound (iv) of the present invention.

The heat-sensitive recording material of the present invention will be described in detail hereinafter.

The heat-sensitive recording material of the present invention comprises a substrate on which a heat-sensitive recording layer is provided. The heat-sensitive recording material may include other layers if needed. Heat-sensitive recording layer The heat-sensitive recording layer contains a coupler and a diazonium salt compound, and if necessary, other components.

Coupler

The coupler contained in the heat-sensitive recording layer contains at least one of pyrrolo[1,2-a]pyrimidine compounds represented by general formula (1). A single pyrrolo [1,2-a]pyrimidine compound or two or more types of such compounds may be used.

The coupler in the present invention is involved in a coupling reaction with a diazo compound in basic atmosphere and/or neutral atmosphere to form a dye. The coupler in the present invention can be used together with known couplers according to various objects such as hue control and the like. Examples of couplers to be used together with the coupler of the present invention include a so-called active methylene compound having a methylene group adjacent to a carbonyl group, phenol derivative, naphthol derivative and the like. Specific examples thereof include the following compounds. These couplers are used in a range corresponding to the objects of the present invention.

Particularly preferable examples of the coupler which can be used together with the coupler of the present invention include resorcin, phloroglucinol, 2,3-dihydroxynaphthalene, sodium 2,3-dihydroxynaphthalene-6-sulfonate, 1-hydroxy-2-naphthoic morpholinopropylamide, sodium 2-hydroxy-4-naphthalenesulfonate, 2-hydroxy-3-naphthalenesulfonic anilide, 2-hydroxy-3-naphthalenesulfonic morpholinopropylamide, 2-hydroxy-3-naphthalenesulfonic 2-ethylhexyloxypropylamide, 2-hydroxy-3-naphthalenesulfonic 2-ethylhexylamide, 5-acetamide-1-naphthol, sodium 1-hydroxy-8-acetamidenaphthalene-3,6-disulfonate, 1-hydroxy-8-acetamidenaphthalene-3,6-disulfonic dianilide, 1,5-dihydroxynaphthalene, 2-hydroxy-3-naphthoic morpholinopropylamide, 2-hydroxy-3-naphthoic octylamide, 2-hydroxy-3-naphthoic anilide, 5,5-dimethyl-1,3-cyclohexanedione, 1,3-cyclopentanedione, 5-(2-n-tetradecyloxyphenyl)-1,3-cyclohexanedione, 5-phenyl-4-methoxycarbonyl-1,3-cyclohexanedione, 5-(2, 5-di-n-octyloxyphenyl)-1,3-cyclohexanedione, N,N'-dicyclohexylbarbituric acid, N,N'-di-n-dodecylbarbituric acid, N-n-octyl-N'-n-octadecylbarbituric acid, N-phenyl-N'-(2,5-di-n-octyloxyphenyl)barbituric acid, N,N'-bis (octadecyloxycarbonylmethyl)barbituric acid, 1-phenyl-3-methyl-5-pyrazolone, 1-(2,4,6-trichlorophenyl)-3-anilino-5-pyrazolone, 1-(2,4,6-trichlorophenyl)-3-benzamide-5-pyrazolone, 6-hydroxy-4-methyl-3-cyano-1-(2-ethylhexyl)-2-pyridone, 2,4-bis-(benzoylacetamide)toluene, 1,3-bis- (pivaloylacetamidemethyl)benzene, benzoylacetonitrile, thenoylacetonitrile, acetacetanilide, benzoylacetanilide, pivaloylacetanilide, 2-chloro-5-(N-n-butylsulfamoyl)-1-pivaloylacetamidebenzene, 1-(2-ethylhexyloxypropyl)-3-cyano-4-methyl-6-hydroxy-1,2-dihydropyridine-2-one, 1-(dodecyloxypropyl)-3-acetyl-4-methyl-6-hydroxy-1,2-dihydropyridine-2-one, 1-(4-n-octyloxyphenyl)-3-tert-butyl-5-aminopyrazole, and the like.

Details of such couplers are described in JP-A Nos. 4-201483, 7-223367, 7-223368, 7-323660, Japanese Patent Application Nos. 5-278608, 5-297024, 6-18669, 6-18670, 7-316280, 8-027095, 8-027096, 8-030799, 8-12610, 8-132394, 8-358755, 8-358756, 9-069990 and the like.

The added amount of the coupler in the heat-sensitive recording layer is from 0.02 to 5 g/m² of the heat-sensitive recording layer, and preferably from 0.1 to 4 g/m² in view of the effects. An added amount of less than 0.02 g/m² is not preferable from the standpoint of the color-forming property, and an added amount of over 5 g/m² is not preferable from the standpoint of suitability for coating.

A water-soluble polymer may be added to the other components of the coupler used in the present invention, and all of these components may be dispersed in a solid state by a sand mill or the like. Further, the coupler may be used, together with a suitable emulsification assistant, as an emulsifier. The solid state dispersing method and emulsifying method are not particularly restricted, and conventionally known methods can be used. Details of such methods are described in JP-A Nos. 59-190886, 2-141279 and 7-17145.

Diazonium salt Compound

The diazonium salt compound used in the present invention is a compound represented by the following general formula:

$$Ar-N_2^+X^-$$

(wherein Ar represents an aromatic moiety, and $X^-$ represents an acid anion). The diazonium salt compound causes a coupling reaction with a coupler due to heating so as to form color, and is decomposed by light. The maximum absorption wavelength thereof can be controlled by the position and type of the substituent on the Ar moiety.

Specific examples of the diazonium forming a salt include 4-(p-tolylthio)-2,5-butoxybenzenediazonium, 4-(4-chlorophenylthio)-2,5-dibutoxybenzenediazonium, 4-(N,N-dimethylamino)benzenediazonium, 4-(N,N-diethylamino) benzenediazonium, 4-(N,N-dipropylamino) benzenediazonium, 4-(N-methyl-N-benzylamino) benzenediazonium, 4-(N,N-dibenzylamino) benzenediazonium, 4-(N-ethyl-N-hydroxyethylamino) benzenediazonium, 4-(N,N-diethylamino)-3-methoxybenzenediazonium, 4-(N,N-dimethylamino)-2-methoxybenzenediazonium, 4-(N-benzoylamino)-2,5-diethoxybenzenediazonium, 4-morpholino-2,5-dibutoxybenzenediazonium, 4-anilinobenzenediazonium,4-[N-(4-methoxybenzoyl)amino]-2,5-diethoxybenzenediazonium, 4-pyrrolidino-3-ethylbenzenediazonium, 4-[N-(1-methyl-2-(4-methoxyphenoxy)ethyl)-N-hexylamino]-2-hexyloxybenzenediazonium, 4-[N-(2-(4-methoxyphenoxy) ethyl)-N-hexylamino]-2-hexyloxybenzenediazonium, 2-(1-ethylpropyloxy)-4-[di-(di-n-butylaminocarbonylmethyl) amino]benzenediazonium, 2-benzylsulfonyl-4-[N-methyl-N-(2-octanoyloxydiethyl)]aminobenzenediazonium and the like.

The maximum absorption wavelength $\lambda_{max}$ of the diazonium salt compound used in the present invention is preferably 450 nm or less from the standpoint of effects, and more preferably from 290 to 440 nm. Diazonium salt compounds having $\lambda_{max}$ higher than the above wavelength range are not preferable from the standpoint of storability before storage. Diazonium salt compounds having a $\lambda_{max}$ lower than the above wavelength range are not preferable from the standpoints of image fixing property, image storability, and hue of the formed cyan color when the diazonium salt compound is used in combination with a coupler.

The diazonium salt compound used in the present invention preferably has a carbon number of 12 or more, solubility in water of 1% or less, and solubility in ethyl acetate of 5% or more.

Among these diazonium salt compounds, it is more preferable to use diazonium salt compounds represented by the above general formulae (2) to (4) from the standpoints of hues of the dyes, image storability and image fixing property.

In general formula (2), Ar represents a substituted or unsubstituted aryl group.

Examples of the substituent include an alkyl group, alkoxy group, alkylthio group, aryl group, aryloxy group, arylthio group, acyl group, alkoxycarbonyl group, carbamoyl group, carboamide group, sulfonyl group, sulfamoyl group, sulfonamide group, ureide group, halogen group, amino group, heterocyclic group and the like. These substituents may further be substituted.

As the aryl group represented by Ar, an aryl group having 6 to 30 carbon atoms is preferable, and examples thereof include, but are not limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 4-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy) phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl) phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Further, these groups may further be substituted by an alkyloxy group, alkylthio group, substituted phenyl group, cyano group, substituted amino group, halogen atom, heterocyclic group or the like.

Each of $R^{11}$ and $R^{12}$ represents a substituted or unsubstituted alkyl group, or a substituted or unsubstituted aryl group. $R^{11}$ and $R^{12}$ may be the same or different from each other.

Examples of the substituent include, but are not limited to, an alkoxy group, alkoxycarbonyl group, alkylsulfonyl group, substituted amino group, substituted amide group, aryl group, aryloxy group and the like.

When each of $R^{11}$ and $R^{12}$ represents an alkyl group, an alkyl group having 1 to 18 carbon atoms is preferably used as the alkyl group. Examples thereof include a methyl group, trifluoromethyl group, ethyl group, propyl group, isopropyl group, butyl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy) propyl group, acetylaminoethyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group and the like.

When each of $R^{11}$ and $R^{12}$ represents an aryl group, an aryl group having 6 to 30 carbon atoms is preferably used as the aryl group. Examples thereof include, but are not limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. These groups may further be substituted by an alkyloxy group, alkylthio group, substituted phenyl group, cyano group, substituted amino group, halogen atom, heterocyclic group or the like.

In general formula (3), $R^{14}$, $R^{15}$ and $R^{16}$ each independently represents a substituted or unsubstituted alkyl group, or a substituted or unsubstituted aryl group.

Examples of the substituents include an alkyl group, alkoxy group, alkylthio group, aryl group, aryloxy group, arylthio group, acyl group, alkoxycarbonyl group, carbamoyl group, carboamide group, sulfonyl group, sulfamoyl group, sulfonamide group, ureide group, halogen group, amino group, heterocyclic group and the like.

When each of $R^{14}$, $R^{15}$ and $R^{16}$ represents an alkyl group, an alkyl group having 1 to 18 carbon atoms is preferably used as the alkyl group. Examples thereof include a methyl group, trifluoromethyl group, ethyl group, propyl group, isopropyl group, butyl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy) propyl group, acetylaminoethyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group, 1-methyl-2-(4-methoxyphenoxy)ethyl group, di-n-butylaminocarbonylmethyl group, di-n-octylaminocarbonylmethyl group and the like.

When each of $R^{14}$, $R^{15}$ and $R^{16}$ represents an aryl group, an aryl group having 6 to 30 carbon atoms is preferably used as the aryl group, and examples thereof include, but are not limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy) phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl) phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Further, these groups may further be substituted by an alkyloxy group, alkylthio group, substituted phenyl group, cyano group, substituted amino group, halogen atom, heterocyclic group or the like.

In general formula (3), Y represents a hydrogen atom or an $-OR^{13}$ group. In the $-OR^{13}$ group, $R^{13}$ represents a substituted or unsubstituted alkyl group, or a substituted or unsubstituted aryl group.

Examples of the substituents include an alkyl group, alkoxy group, alkylthio group, aryl group, aryloxy group, arylthio group, acyl group, alkoxycarbonyl group, carbamoyl group, carboamide group, sulfonyl group, sulfamoyl group, sulfonamide group, ureide group, halogen group, amino group, heterocyclic group and the like. From the standpoint of control of hue, Y preferably represents a hydrogen atom or an alkyloxy group in which $R^{13}$ is an alkyl group.

When $R^{13}$ in the $-OR^{13}$ group represents an alkyl group, an alkyl group having 1 to 18 carbon atoms is preferably used as the alkyl group, and examples thereof include a methyl group, trifluoromethyl group, ethyl group, propyl group, isopropyl group, butyl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy) propyl group, acetylaminoethyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group and the like.

When $R^{13}$ in the —$OR^{13}$ group represents an aryl group, an aryl group having 6 to 30 carbon atoms is preferably used as the aryl group, and examples thereof include, but are not limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Further, these groups may further be substituted by an alkyloxy group, alkylthio group, substituted phenyl group, cyano group, substituted amino group, halogen atom, heterocyclic group or the like.

In general formula (4), $R^{17}$ and $R^{18}$ each independently represents a substituted or unsubstituted alkyl group, or a substituted or unsubstituted aryl group. $R^{17}$ and $R^{18}$ may be the same or different.

Examples of the substituents include an alkyl group, alkoxy group, alkylthio group, aryl group, aryloxy group, arylthio group, acyl group, alkoxycarbonyl group, carbamoyl group, carboamide group, sulfonyl group, sulfamoyl group, sulfonamide group, ureide group, halogen group, amino group, heterocyclic group and the like.

When each of $R^{17}$ and $R^{18}$ represents an alkyl group, an alkyl group having 1 to 18 carbon atoms is preferably used as the alkyl group, and examples thereof include, but are not limited to, a methyl group, trifluoromethyl group, ethyl group, propyl group, isopropyl group, butyl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy)propyl group, acetylaminoethyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group and the like.

When each of $R^{17}$ and $R^{18}$ represents an aryl group, an aryl group having 6 to 30 carbon atoms is preferably used as the aryl group, and examples thereof include a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Further, these groups may further be substituted by an alkyloxy group, alkylthio group, substituted phenyl group, cyano group, substituted amino group, halogen atom, heterocyclic group or the like.

Ingeneral formulae (2) to (4), $X^-$ representsanacidanion. Examples of the acid anion include polyfluoroalkylcarboxylic acids having 1 to 9 carbon atoms, polyfluoroalkylsulfonic acids having 1 to 9 carbon atoms, boron tetrafluoride, tetraphenylboron, hexafluorophosphoric acid, aromatic carboxylic acids, aromatic sulfonic acids and the like. Hexafluorophosphoric acid is preferable in view of crystallinity.

Examples of the diazonium salt compounds represented by general formulae (2) to (4) include, but are not limited to, the following compounds.

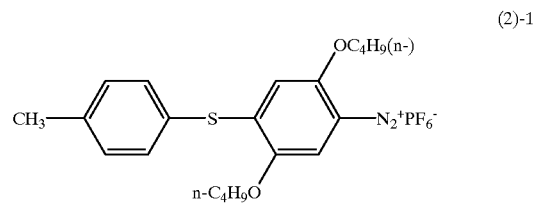

(2)-1

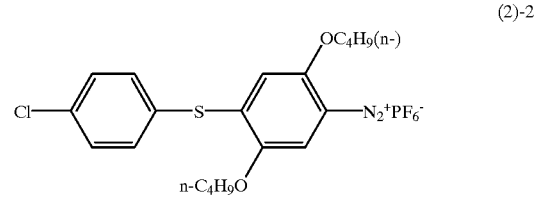

(2)-2

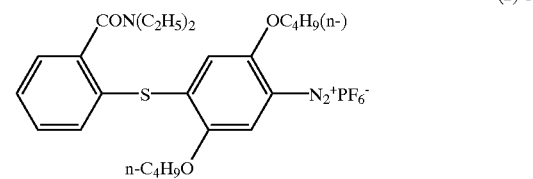

(2)-3

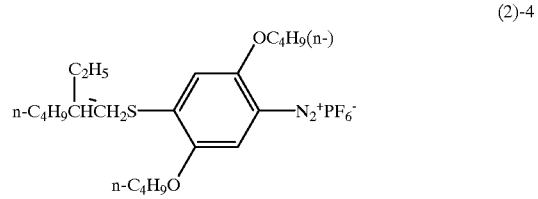

(2)-4

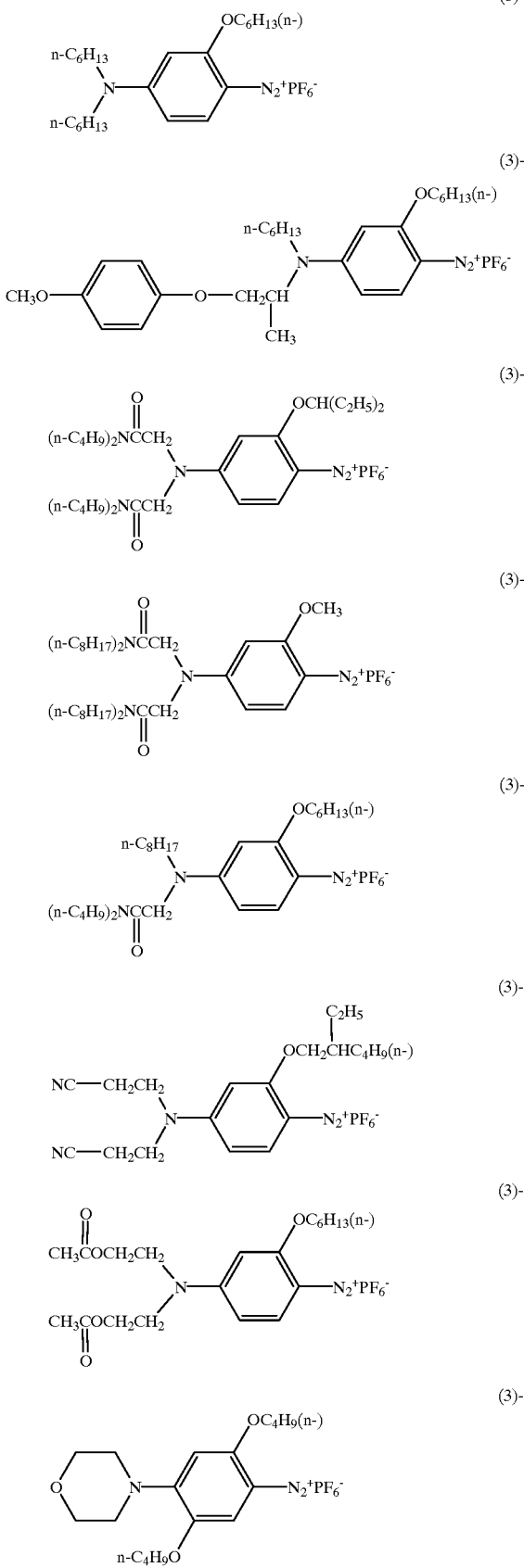
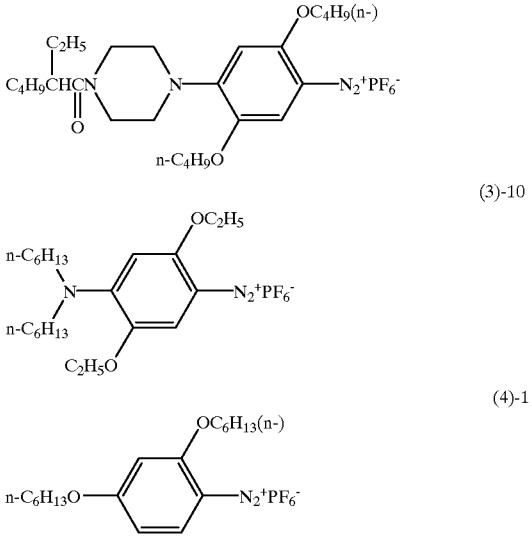

In the present invention, the diazonium salt compounds represented by general formulae (2) to (4) may be used alone, or a combination of two or more types may be used. Further, the diazonium salt compounds represented by general formulae (2) to (4) may also be used together with known diazonium salt compounds in accordance with various objects such as hue control and the like.

The content of the diazonium salt compound used in the present invention in the heat-sensitive recording layer is preferably from 0.02 to 3 g/m², and more preferably from 0.1 to 2 g/m².

The diazonium salt compound used in the present invention is preferably encapsulated in microcapsules from the standpoint of storability. The method for preparing the microcapsules is not particularly limited, and the microcapsules can be prepared by a conventionally known method using a wall material such as gelatin, polyurea, polyurethane, polyimide, polyester, polycarbonate, melamine or the like. Of these wall materials, polyurethane and polyurea are preferable from the standpoints of color-developing property and storability. Details of methods for preparing microcapsules are described in JP-A No. 2-141279 and the like.

Further, when preparing microcapsules, an organic solvent having a high boiling point may be used as disperson solvent. The organic solvent is not particularly restricted, and conventionally known solvents such as alkyl phthalate, phosphate, citrate, benzoate, alkylamide, fatty ester, trimesilate and the like can be used. Details thereof are described in JP-A No. 7-17145 and the like.

Other components

In the present invention, it is preferable to use organic bases such as tertiary amines, piperidines, piperazines, amidines, formamidines, pyridines, guanidines, morpholines and the like in order to accelerate the coupling reaction.

Examples of these organic bases include piperazines such as N,N'-bis(3-phenoxy-2-hydroxypropyl)piperazine, N,N'-bis[3-(p-methylphenoxy)-2-hydroxypropyl]piperazine, N,N'-bis[3-(p-methoxyphenoxy)-2-hydroxypropyl] piperazine, N,N'-bis(3-phenylthio-2-hydroxypropyl) piperazine, N,N'-bis[3-(β-naphthoxy)-2-hydroxypropyl] piperazine, N-3-(β-naphtoxy)-2-hydroxypropyl-N'-methylpiperazine, 1,4-bis{[3-(N-methylpiperadino)-2- hydroxy]propyloxy}benzene and the like, morpholines such as N-[3-(β-naphtoxy)-2-hydroxy]propylmorpholine, 1,4-bis[(3-morpholino-2-hydroxy)propyloxy]benzene, 1,3-bis[(3-morpholino-2-hydroxy)propyloxy]benzene and the like, piperidines such as N-(3-phenoxy-2-hydroxypropyl) piperidine, N-dodecylpiperidine and the like, triphenylguanidine, tricyclohexylguanidine, dicyclohexylphenylguanidine, 2-N-methyl-N-benzylaminoethyl 4-hydroxybenzoate, 2-N,N-di-n-butylaminoethyl 4-hydroxybenzoate, 4-(3-N,N-dibutylaminopropoxy)benzenesulfonamide, 4-(2-N,N'-butylaminoethoxycarbonyl)phenoxy acetic amide and the like.

Details thereof are described in JP-A Nos. 57-123086, 60-49991 and 60-94381, Japanese Patent Application Nos. 7-228731, 7-235157 and 7-235158, and the like. These organic bases may be used alone, or two or more types may be used in combination. The amount of the organic base used in the present invention is not particularly limited, and preferably is in the range from 1 to 30 mol per one mol of the diazonium salt compound.

In the present invention, a color-developing assistant can also be added in addition to the pyrrolo[1,2-a]pyridimine compound represented by general formula (1), for the purpose of improving the color-developing property. Examples of the color-developing assistant include phenol derivatives, naphthol derivatives, alkoxy-substituted benzenes, alkoxy-substituted naphthalenes, hydroxy compounds, carboxylic amide compounds, sulfonamide compounds and the like. It is believed that these compounds lower the melting point of the coupler or the basic substance or improve the heat permeability of the microcapsule wall, resulting in high density of the formed color.

Method of Producing Heat-Sensitive Recording Layer

For producing the heat-sensitive recording layer of the present invention, a coating solution containing a diazonium salt compound, the pyrrolo[1,2-a]pyrimidine compound represented by general formula (1) and other additives is prepared, and this solution is coated on a substrate such as paper, synthetic film or the like by a coating method such as bar coating, blade coating, air knife coating, gravure coating, roll coating, spray coating, dip coating, curtain coating or the like, and is dried to obtain a heat-sensitive recording layer having a solid content of 2 to 30 $g/m^2$.

The binder used in the present invention is not particularly limited, and conventionally known binders can be used such as polyvinyl alcohol, hydroxyethylcellulose, methylcellulose, carboxymethylcellulose, gelatin, styrene-acrylic acid copolymer and the like. Details thereof are described in JP-A No. 2-141279 and the like. In addition, various organic or inorganic pigments, various stabilizers, antioxidants and the like can also be added if necessary.

In the heat-sensitive recording material of the present invention, a diazonium salt compound, the pyrrolo[1,2-a]pyrimidine compound represented by general formula (1), and the like may be contained in the same layer, or may be contained in separate layers which are layered one upon the other.

Substrate

Conventionally known substrates can be used for the substrate used in the present invention. Specifically, neutral paper, acidic paper, recycled paper, polyolefin resin-laminated paper, synthetic paper, polyester film, cellulose derivative films such as triacetic cellulose film and the like, polyolefin films such as polystyrene film, polypropylene film, polyethylene film and the like can be used alone, or two or more types can be laminated together for use.

The thickness of the substrate may be from 20 to 200 $\mu$m. Further, there can also be provided an intermediate layer between the substrate and the heat-sensitive recording layer. These are described in JP-A No. 61-54980 and the like.

Other layers and the like

In the heat-sensitive recording layer of the present invention, a protective layer is preferably provided on the heat sensitive-recording layer, and this protective layer is preferably laminated. The protective layer is formed from a water-soluble polymer, a pigment or the like. To achieve both light-resistance and light-stability in this protective layer, a compound having a function of controlling ultraviolet ray transmittance is preferably contained in the protective layer. Details of a heat-sensitive recording material containing a compound having a function of controlling ultraviolet ray transmittance are described in JP-A No. 7-276808.

The heat-sensitive recording material of the present invention can be used as a multi-color heat-sensitive recording material. Details of a multi-color heat-sensitive recording material are described in JP-A Nos. 4-135787, 4-144784, 4-144785, 4-194842, 4-247447, 4-247448, 4-340540, 4-340541, 5-34860 and the like.

Specifically, such a material can be obtained by laminating heat-sensitive recording layers which form colors in different hues. The layer structure is not particularly limited. One example thereof is a multi-color heat-sensitive recording material prepared by laminating two heat-sensitive recording layers (B layer, C layer) obtained by combining two kinds of diazonium salt compounds having different light-sensitive wavelengths with couplers which form colors of different hues by reacting with the respective diazonium salt compounds during heating, and a heat-sensitive recording layer (A layer) obtained by combining an electron donating colorless dye with an electron receiving compound.

Specifically, the material comprises a substrate on which are provided a first heat-sensitive recording layer (A layer) containing an electron donating colorless dye and an electron receiving compound, a second heat-sensitive recording layer (B layer) containing a diazonium salt compound having a maximum absorption wavelength of 360 nm±20 nm and a coupler which forms color by reacting with the diazonium salt compound during heating, and a third heat-sensitive recording layer (C layer) containing a diazonium salt compound having a maximum absorption wavelength of 400 nm±20 nm and a coupler which forms color by reacting with the diazonium salt compound during heating. In this example, if formed color hues in the respective heat-sensitive recording layers are selected such that the three primary colors in subtractive color mixing, yellow, magenta and cyan, are obtained, full color image recording becomes possible.

To record by using this multi-color heat-sensitive recording material, first, the third heat-sensitive recording layer (C layer) is heated to allow the diazonium salt and the coupler contained in the layer to form color. Then, the unreacted diazonium salt compound contained in the C layer is decomposed and fixed by irradiation with light having a wavelength of 400±20 nm. Thereafter, sufficient heat for color-formation of the second heat-sensitive recording layer (B layer) is applied to allow the diazonium salt compound and the coupler contained in the layer to form color. At this time, although the C layer is simultaneously heated significantly, it does not form color since the diazonium salt compound has already decomposed (has been fixed by light) and the color-forming ability is lost. Further, the diazonium salt compound contained in the B layer is decomposed by irradiation with light having a wavelength of 320±20 nm. Lastly, heat sufficient for color-formation of the first heat-sensitive recording layer (A layer) is applied to form color. At this time, although the heat-sensitive recording layers C and B are also heated significantly, they do not form color since the diazonium salt compounds have already decomposed and their color developing abilities are lost.

Further, all of the heat-sensitive recording layers (A layer, B layer and C layer, in this order from the upper layer) can be heat-sensitive recording layers which are obtained by combining three kinds of diazonium salt compounds having different light-sensitive wavelengths, with couplers which form color in different hues by reacting with the respective diazonium salt compounds during heating. In particular, by setting the yellow layer having a low luminosity factor as the lower most layer, effects on images due to roughness on the surface of the substrate can be reduced, and image quality can be improved. When all of the heat-sensitive recording layers (A layer, B layer and C layer) are diazo-based heat-sensitive recording layers, it is necessary to carry out light-fixing of the A layer and the B layer after color-formation. There is no need to carry out light-fixing for the C layer.

Various fluorescent lamps, xenon lamps, mercury lamps and the like may be used as the light source for fixing used in the above-described fixing by light. It is preferable that the emission spectrum approximately coincides with the absorption spectrum of the diazonium salt compound used in the heat-sensitive material since then efficient light-fixing is possible.

Further, when recording the heat-sensitive recording material of the present invention, the heat-sensitive recording material can also be used as a heat-developing type light-sensitive material by which an image can be obtained by exposing the material through an original, decomposing the diazonium salt compounds at portions other than the image formed portions to form a latent image, and thereafter, heating the entire material.

EXAMPLES

The following Examples further illustrate the present invention, but do not limit the scope thereof. In the examples, all "parts" are "parts by weight". Pyrrolo[1,2-a]pyrimidine compound represented by general formula (1)

Hereinafter, the numbers in parentheses after "coupler" are the numbers in parentheses in Tables 1 though 5 in which specific examples of couplers are listed.

Example 1 Synthesis of Coupler (1)

5 g of 2-amino-7-cyano-6-phenyl-pyrrolo[1,2-a]pyrimidine-4-one was dissolved in 20 ml of N,N-dimethylacetamide and the resulting reaction solution was cooled by ice to 0° C. To this was slowly added 2 g of sodium hydride (content: 60%) and the solution was stirred for 15 minutes while being cooled by ice. Then, 6.5 g of 2-ethyl-hexylic acid chloride was slowly added dropwise, and the solution was stirred for 1 hour while being cooled by ice. Further, the solution was stirred for 4 hours at room temperature, and thereafter, the reaction product was poured in ice water, and neutralized with dilute hydrochloric acid. Then, the reaction product was extracted with 100 ml of ethyl acetate, washed with a saturated sodium chloride solution, and dried over magnesium sulfate. Thereafter, the solvent was distilled off under reduced pressure. The residue was purified by silica gel chromatography, toobtain4.5 gof apaleyellowcrystal (coupler (1)).

The melting point was 155° C. The results of NMR are given below.

$^1$H (CDCl$_3$); δ: 0.89 to 1.80 (14H, m); 2.42 (1H, m); 5.53 (1H, s); 7.39 to 7.71 (4H, m); 7.72 (2H, d, J=6.0 Hz); 9.42 (1H, s); 13.16 (1H, s).

Example 2 Synthesis of Coupler (4)

5 g of 2-amino-7-cyano-6-phenyl-pyrrolo[1,2-a]pyrimidine-4-one was dissolved in 20 ml of N,N-dimethylacetamide and the resulting reaction solution was cooled to 0° C. To this was slowly added 1.6 g of sodium hydride (content: 60%) and the solution was stirred for 15 minutes while being cooled by ice. Then, 7.5 g of 2-ethyl-hexyl-chloroformate was slowly added dropwise, and the solution was stirred for 30 minutes while being cooled by ice. Further, the solution was stirred for 3 hours at 45 to 55° C., and thereafter, the reaction product was poured in ice water, and neutralized with dilute hydrochloric acid. Then, the reaction product was extracted with 70 ml of ethyl acetate, washed with a saturated sodium chloride solution, and dried over magnesium sulfate. Thereafter, the solvent was distilled off under reduced pressure. The residue was purified by silica gel chromatography, to obtain 5.3 gof awhitecrystal (coupler (4)).

The melting point was 178° C. The results of NMR are given below.

$^1$H (CDCl$_3$, 300 Hz); δ: 0.85 to 1.38 (14H, m); 1.62 (1H, m); 4.21 (2H, m); 5.60 (1H, s); 7.27 to 7.51 (4H, m); 7.71 (2H, d, J=6.0 Hz); 9.12 (1H, s); 12.04 (1H, s).

Example 3 Synthesis of Coupler (18)

3 g of 2-amino-7-ethoxycarbonyl-6-phenyl-pyrrolo[1,2-a]pyrimidine-4-one was dissolved in 15 ml of tetrahydrofuran (THF) and the resulting reaction solution was cooled to 0° C. To this was slowly added 1.2 g of sodium hydride (content: 60%) and the solution was stirred for 15 minutes while being cooled by ice. Then, 3.3 g of 2-ethyl-hexylic acid chloride was slowly added dropwise, and the solution was stirred for 1 hour while being cooled by ice. Further, the solution was stirred for 4 hours at room temperature, and thereafter, the reaction product was poured in ice water, and neutralized with dilute hydrochloric acid. Then, the reaction product was extracted with 100 ml of ethyl acetate, washed with a saturated sodium chloride solution, and dried over magnesium sulfate. Thereafter, the solvent was distilled off under reduced pressure. The residue was purified by silica gel chromatography, to obtain 3.5 g of a white crystal (coupler (18)).

The melting point was 169° C. The results of NMR are given below.

$^1$H (CDCl$_3$, 300 Hz); δ: 0.80 to 1.75 (14H, m); 0.92 (3H, t, J=6.0 Hz); 2.38 (1H, m); 4.33 (2H, q, J=6.0 Hz); 5.55 (1H, s); 7.34 to 7.52 (4H, m); 7.53 (2H, d, J=6.0 Hz); 10.21 (1H, s); 13.72 (1H, s).

Example 4 Synthesis of Coupler (30)

2.5 g of 2-amino-7-[2,6-di-t-butyl-4-methyl]cyclohexyloxycarbonyl-6-phenyl-pyrrolo[1,2-a]pyrimidine-4-one was dissolved in 15 ml of tetrahydrofuran (THF) and the resulting reaction solution was cooled to 0° C. To this was slowly added 0.46 g of sodium hydride (content: 60%) and the solution was stirred for 15 minutes while being cooled by ice. Then, 1.1 g of 2-ethyl-hexyl-chloroformate was slowly added dropwise, and the solutionwas stirred for 30 minutes while being cooled by ice. Further, the solution was stirred for 3 hours at 45 to 55° C., and thereafter, the reaction product was poured in ice water, and neutralized with dilute hydrochloric acid. Then, the reaction product was extracted with 50 ml of ethyl acetate, washed with a saturated sodium chloride solution, and dried over magnesium sulfate. Thereafter, the solvent was distilled off under reduced pressure. The residue was purified by silica gel chromatography, to obtain 2.3 g of a white crystal (coupler (30)).

The melting point was 144° C. The results of NMR are given below.

$^1$H (CDCl$_3$, 300 Hz); δ: 0.53 to 1.81 (43H, m); 4.18 (2H, m); 5.55 (1H, s); 5.96 (1H, s); 7.19 (1H, s); 7.38 to 7.46 (5H, m); 8.89 (1H, s); 13.91 (1H, S).

Example 5 Synthesis of Coupler (31)

3 g of 2-amino-7-[2,6-di-t-butyl-4-methyl] cyclohexyloxycarbonyl-6-phenyl-pyrrolo[1,2-a]pyrimidine-4-one was dissolved in 15 ml of tetrahydrofuran (THF) and the resulting reaction solution was cooled to 0° C. To this was slowly added 0.56 g of sodium hydride (content: 60%) and the solution was stirred for 15 minutes while being cooled by ice. Then, 0.7 g of methyl-chloroformate was slowly added dropwise, and the solution was stirred for 30 minutes while being cooled by ice. Further, the solution was stirred for 3 hours at 45 to 55° C., and thereafter, the reaction product was poured in ice water, and neutralized with dilute hydrochloric acid. Then, the reaction product was extracted with 50 ml of ethyl acetate, washed with a saturated sodium chloride solution, and dried over magnesium sulfate. Thereafter, the solvent was distilled off under reduced pressure. The residue was purified by silica gel chromatography, to obtain 2.7 g of a white crystal (coupler (25)).

2.5 g of the resultant coupler (25) was dissolved in 5 ml of acetonitrile, and to this solution was added 1.2 g of 2-ethylhexylamine, and the mixture was heated under reflux for 2 hours. The solution was cooled to room temperature and the solvent was distilled off under reduced pressure.

15 ml of methanol was added to the residue, and the precipitated crystal was filtered out to obtain 2.7 g of a white crystal (coupler (31)).

The melting point was 144° C. The results of NMR are given below.

$^1$H (DMSO-d$_6$, 300 Hz); δ: 0.56 to 2.02 (43H, m); 3.28 (2H, m); 5.26 (1H, s); 5.98 (1H, s); 6.37 (1H, s); 7.04 (1H, s); 7.37 to 7.42 (5H, m); 10.18 (1H, s); 13.83 (1H, s).

Example 6 Synthesis of Coupler (36)

Coupler (36) was synthesized in the same manner as in Example 3 except that instead of the 2-amino-7-ethoxycarbonyl-6-phenyl-pyrrolo[1,2-a]pyrimidine-4-one used in Example 3, 2-amino-7-[2,6-di-t-butyl-4-methyl] cyclohexyloxycarbonyl-6-[4-chloro-phenyl]-pyrrolo[1,2-a] pyrimidine-4-one was used.

The melting point was 130° C. The results of NMR are given below.

$^1$H (CDCl$_3$, 300 Hz); δ: 0.51 to 1.77 (42H, m); 2.41 (1H, m); 5.58 (1H, s); 5.99 (1H, S); 7.15 (1H, s); 7.32 (2H, d, J=6.0 Hz); 7.40 (2H, d, J=6.0 Hz); 9.43 (1H, s); 13.63 (1H, s).

Example 7 Synthesis of Coupler (39)

Coupler (39) was synthesized in the same manner as in Example 3 except that instead of the 2-amino-7-ethoxycarbonyl-6-phenyl-pyrrolo[1,2-a]pyrimidine-4-one used in Example 3, 2-amino-7-[2,6-di-t-butyl-4-methyl] cyclohexyloxycarbonyl-6-[3,4-dichloro-phenyl]-pyrrolo[1, 2-a]pyrimidine-4-one was used, and instead of the 2-ethyl-hexylic acid chloride, pivaloyl chloride was used.

The melting point was 223° C. The results of NMR are given below.

$^1$H (DMSOd$_6$, 300 Hz); δ: 0.51 to 1.18 (8H, m); 0.84 (9H, s); 1.30 (9H, s); 5.84 (1H, s); 5.93 (1H, S); 7.36 (1H, d, J=6.0 Hz); 7.48 (1H, s); 7.73 (2H, d, J=6.0 Hz); 10.51 (1H, s); 13.01 (1H, s).

Heat-sensitive Recording Material

Example 8
Preparation of Microcapsule Liquid A

To 19 g of ethyl acetate were added 2.8 parts of a diazonium salt (example compound (3)-1, maximum absorption wavelength: 370 nm) and 10 parts of tricresyl phosphate, and they were mixed uniformly. Then, to this mixture was added 7.6 parts of Takenate D-110N (manufactured by Takeda Chemical Industries Ltd.) as a wall agent, and they were mixed uniformly to obtain liquid I.

Then, to this liquid I were added 46 parts of a 8% by weight aqueous solution of phthalated gelatin, 17.5 parts of water, and 2 parts of a 10% aqueous solution of sodium dodecylbenzenesulfonate, and the mixture was emulsified and dispersed at 10000 r.p.m. for 10 minutes at a temperature of 40° C. To the resultant emulsion was added 20 parts of water and the mixture was made uniform, and thereafter, a microcaplsule forming reaction was made to take place for 3 hours at 40° C. while stirring to obtain microcapsule liquid A. The average particle diameter of the microcapsule was from 0.7 to 0.8 μm.

Preparation of Coupler Emulsified Liquid B

To 10.5 parts of ethyl acetate were added 3.0 parts of coupler (1), 3.0 parts of triphenylguanidine, 0.5 parts of tricresyl phosphate and 0.24 parts of diethyl maleate to obtain liquid II.

Then, 49 parts of a 15% by weight aqueous solution of lime-treated gelatin, 9.5 parts of a 10% aqueous solution of sodium dodecylbenzenesulfonate and 35 parts of water were mixed uniformly at 40° C., and to this mixture was added liquid II, and the mixture was emulsified and dispersed at 10000 r.p.m. for 10 minutes at a temperature of 40° C. by using a homogenizer. The resultant emulsion was stirred for 2 hours at 40° C. to remove ethyl acetate, then, water was added in an amount (weight) corresponding to the vaporized ethyl acetate and water, so as to obtain coupler emulsified liquid B.

Preparation of Heat-Sensitive Recording Layer Coating Liquid C 3.6 parts of microcapsule liquid A, 3.3 parts of water and 9.5 parts of coupler emulsified liquid B were uniformly mixed to obtain heat-sensitive recording layer coating liquid C. Preparation of protective layer coating liquid D 100 parts of a 6% aqueous solution of itaconic acid-modified polyvinyl alcohol (trade name: KL-318, manufactured by Kuraray Co., Ltd.) and 10 parts of a 30% dispersion of an epoxy-modified polyamide (trade name: FL-71, manufactured by Toho Chemical Industry Co., Ltd.) were mixed together, and into this was mixed uniformly 15 parts of a 40% dispersion of zinc stearate (trade name: Hydrin Z, manufactured by Chukyo Yushi K.K.) to obtain protective layer coating liquid D.

Coating

On a substrate for photographic printing paper which substrate had been formed by laminating polyethylene onto a high quality paper, the heat-sensitive recording layer coating liquid C and the protective layer coating liquid D were respectively coated and dried at 50° C. in that order to obtain the intended heat-sensitive recording material. The coated amounts in terms of solid components were 8.0 g/m² and 1.2 g/m² respectively.

The resultant heat-sensitive recording materials were subjected to the following tests and evaluated.

Color-Developing Test

A sample was thermally printed using a thermal head (KST type) manufactured by Kyocera Corp. with the pulse width and power applied to the thermal head having been determined such that the recording energy per unit area was 50 mJ/mm². Thereafter, the entire surface of the sample was irradiated by light for 15 seconds by using an ultraviolet ray lamp having an emission center wavelength of 365 nm and an output of 40 W. The densities of the image portions and ground portions of the resultant sample were measured by a Macbeth densitometer.

Image Light-Resistance Test

By using a fluorescent lamp light-resistance tester, the image portions, which had been color-developed by using a thermal head (KST type) manufactured by Kyocera Corp., were irradiated by light continuously for 24 hours at 32000 lux, and thereafter, the density of the image portions was measured. The higher the density of the image portions after irradiation, the more excellent the image light-resistance.

Image Fixing Property Test

For testing the image fixing property, the ground portions (non-printed portions) of the fixed sample were thermally printed by using a thermal head (KST type) manufactured by Kyocera Corp. with the pulse width and power applied to the thermal head having been determined such that the recording energy per unit area was 40 mJ/mm², and the change in density was measured. The lower the density after printing, the more excellent the image fixing property.

Hue Test

The reflection spectrum within a wavelength range from 400 to 475 nm of the image portions, which had been color-formed by using a thermal head (KST type) manufactured by Kyocera Corp., were measured by a UV/VIS photospectroscope.

A lower measured absorption means that an excellent cyan color in which there is little yellow has been obtained.

Example 9

A heat-sensitive recording material of Example 9 was prepared and evaluated in the same manner as in Example 8, except that the emulsified liquid was obtained by using coupler (4) instead of the coupler (1) used in Example 8.

Example 10

A heat-sensitive recording material of Example 10 was prepared and evaluated in the same manner as in Example 8 except that the emulsified liquid was obtained by using coupler (18) instead of the coupler (1) used in Example 8.

Examlpe 11

A heat-sensitive recording material of Example 11 was prepared and evaluated in the same manner as in Example 8 except that the microcapsule liquid was prepared by using example compound (3)-2 (maximum absorption wavelength: 370 nm) instead of the diazonium salt (example compound (3)-1) used in Example 8.

Examlpe 12

A heat-sensitive recording material of Example 12 was prepared and evaluated in the same manner as in Example 8 except that the emulsified liquid was obtained by using coupler (30) instead of the coupler (1) used in Example 8.

Examlpe 13

A heat-sensitive recording material of Example 13 was prepared and evaluated in the same manner as in Example 8 except that the emulsified liquid was obtained by using coupler (31) instead of the coupler (1) used in Example 8.

Examlpe 14

A heat-sensitive recording material of Example 14 was prepared and evaluated in the same manner as in Example 8 except that the emulsified liquid was obtained by using coupler (36) instead of the coupler (1) used in Example 8.

Examlpe 15

A heat-sensitive recording material of Example 15 was prepared and evaluated in the same manner as in Example 8 except that the emulsified liquid was obtained by using coupler (39) instead of the coupler (1) used in Example 8.

Comparative Example 1

A heat-sensitive recording material of Comparative Examlpe 1 was prepared and evaluated in the same manner as in Example 8 except that the emulsified liquid was obtained by using a comparative coupler represented by the following formula instead of the coupler (1) used in Example 8.

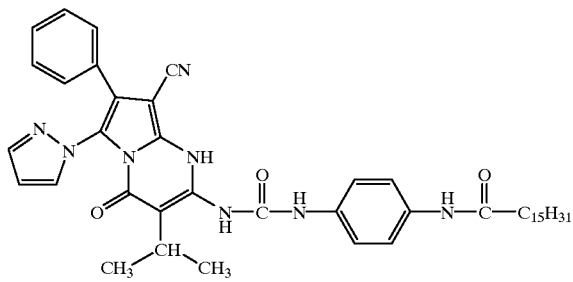

Values of $\lambda_{max}$ and results of the image light-resistance test and image fixing property test of the image portions are given in Table 6. Data on the absorbance (wavelength: 400 to 475 nm) of the image portions are given in Table 7.

TABLE 6

| | | Image light-resistance test Density of image portions | | Image fixing property test Density of ground portions | |
|---|---|---|---|---|---|
| | Color-formed image $\lambda_{max}$ | Before irradiation | After irradiation | Before printing | After printing |
| Example 8 | 672 | 1.60 | 1.31 | 0.05 | 0.08 |
| Example 9 | 668 | 1.63 | 1.28 | 0.05 | 0.08 |
| Example 10 | 664 | 1.54 | 1.30 | 0.06 | 0.07 |
| Example 11 | 667 | 1.56 | 1.27 | 0.05 | 0.07 |
| Example 12 | 661 | 1.54 | 1.28 | 0.05 | 0.07 |
| Example 13 | 659 | 1.56 | 1.27 | 0.06 | 0.08 |
| Example 14 | 669 | 1.53 | 1.29 | 0.05 | 0.07 |
| Example 15 | 670 | 1.54 | 1.30 | 0.05 | 0.07 |
| Comparative example 1 | 648 | 0.45 | 0.08 | 0.05 | 0.14 |

TABLE 7

| | Absorbance | | |
|---|---|---|---|
| | Wavelength (400 nm) | Wavelength (450 nm) | Wavelength (475 nm) |
| Example 8 | 0.20 | 0.16 | 0.12 |
| Example 9 | 0.21 | 0.15 | 0.11 |
| Example 10 | 0.19 | 0.15 | 0.12 |
| Example 11 | 0.21 | 0.17 | 0.11 |
| Example 12 | 0.18 | 0.15 | 0.11 |
| Example 13 | 0.20 | 0.17 | 0.12 |
| Example 14 | 0.19 | 0.15 | 0.11 |
| Example 15 | 0.19 | 0.16 | 0.11 |
| Comparative example 1 | 0.28 | 0.24 | 0.21 |

From these results, it can be understood that a heat-sensitive recording material using as a coupler a pyrrolo[1,2-a]pyrimidine compound represented by general formula (1) of the present invention has high color-formed density. Further, even after irradiation with a fluorescent lamp, there is little decrease in density in the image portions and image light-resistance is excellent. Moreover, when the ground portions of a sample which has been subjected to image fixing are again thermally printed, there is little color-formation and the image fixing property is excellent. Also, there is little absorption of yellow color, and an excellent cyan color can be obtained.

According to the present invention, there is provided a novel pyrrolo[1,2-a]pyrimidine compound which, when coupled with a diazonium salt as a coupler, can provide excellent color-forming property and can provide a cyan dye which has low absorption of yellow color. Further, in accordance with the present invention, by combining the pyrrolo[1,2-a]pyrimidine compound with a diazonium salt compound, there can be provided a novel cyan color-forming type diazo heat-sensitive recording material having excellent shelf life, image light-resistance and image fixing property in addition to the above-described properties.

What is claimed is:

1. A pyrrolo[1,2-a]pyrimidine compound represented by following general formula (1):

General formula (1)

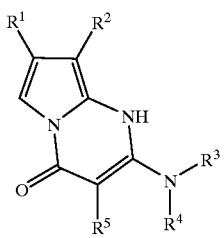

(wherein, in general formula (1), $R^1$ represents an aryl group, alkyl group, carbamoyl group, alkoxycarbonyl group or aryloxycarbonyl group; $R^2$ represents an alkoxycarbonyl group, aryloxycarbonyl group or cyano group; $R^3$ and $R^4$ each independently represents a hydrogen atom, aryl group, alkyl group, acyl group, carbamoyl group, alkoxycarbonyl group, aryloxycarbonyl group, alkylsulfonyl group, arylsulfonyl group, sulfamoyl group, alkylphosphoryl group or arylphosphoryl group; $R^5$ represents a hydrogen atom, halogen atom, cyano group, acyl group, carbamoyl group, alkoxycarbonyl group, aryloxycarbonyl group, acyloxy group, sulfamoyl group, alkylsulfonyl group, arylsulfonyl group, alkylphosphoryl group or arylphosphoryl group).

2. A heat-sensitive recording material comprising a substrate, and on said substrate, a heat-sensitive recording layer containing a diazonium salt compound and a coupler which forms color by reacting with the diazonium salt compound during heating, wherein the coupler contains at least one of the pyrrolo[1,2-a]pyrimidine compounds represented by general formula (1) of claim 1.

3. A heat-sensitive recording material according to claim 2, wherein the maximum absorption wavelength $\lambda_{max}$ of the diazonium salt compound is 450 nm or less.

4. A heat-sensitive recording material according to claim 2, wherein the diazonium salt compound is at least one of compounds represented by following general formulae (2) to (4):

General formula (2)

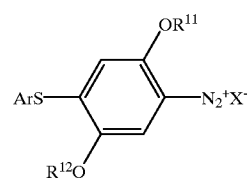

(wherein, in general formula (2), Ar represents a substituted or unsubstituted aryl group, and $R^{11}$ and $R^{12}$ each independently represents a substituted or unsubstituted alkyl group or a substituted or unsubstituted aryl group; $R^{11}$ and $R^{12}$ may be the same or different; and $X^-$ represents an acid anion);

General formula (3)

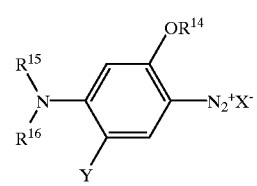

(wherein, in general formula (3), $R^{14}$, $R^{15}$ and $R^{16}$ each independently represents a substituted or unsubstituted alkyl group or a substituted or unsubstituted aryl group; $R^{14}$, $R^{15}$ and $R^{16}$ may be the same or different; Y represents a hydrogen atom or an —$OR^{13}$ group; $R^{13}$ represents a substituted or unsubstituted alkyl group or a substituted or unsubstituted aryl group; and $X^-$ represents an acid anion);

General formula (4)

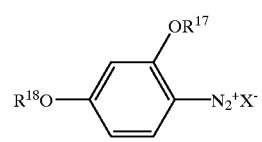

(wherein, in general formula (4), $R^{17}$ and $R^{18}$ each independently represents a substituted or unsubstituted alkyl group or a substituted or unsubstituted aryl group; and $X^-$ represents an acid anion).

5. A heat-sensitive recording material according to claim 3, wherein the diazonium salt compound is at least one of compounds represented by the general formulae (2) to (4).

6. A heat-sensitive recording material according to claim 2, wherein the diazonium salt compound is encapsulated in microcapsules.

7. A heat-sensitive recording material according to claim 3, wherein the diazonium salt compound is encapsulated in microcapsules.

8. A heat-sensitive recording material according to claim 4, wherein the diazonium salt compound is encapsulated in microcapsules.

9. A heat-sensitive recording material according to claim 6, wherein capsule walls of the microcapsules comprise polyurethane and/or polyurea.

10. A heat-sensitive recording material according to claim 7, wherein capsule walls of the microcapsules comprise polyurethane and/or polyurea.

11. A heat-sensitive recording material according to claim 8, wherein capsule walls of the microcapsules comprise polyurethane and/or polyurea.

* * * * *